United States Patent
Swab et al.

(10) Patent No.: US 6,911,172 B2
(45) Date of Patent: Jun. 28, 2005

(54) METHOD OF MANUFACTURING EYEWEAR

(75) Inventors: Gregory Swab, Tulsa, OK (US); James E. Malackowski, Chicago, IL (US); Mikal Greaves, Mountain View, CA (US); Rolf Milesi, Sunnyvale, CA (US); Christine Ligtenberg, San Carlos, CA (US); Thomas Meier, San Jose, CA (US)

(73) Assignee: Q.R. Spex, Inc., Tulsa, OK (US)

( * ) Notice: Subject to any disclaimer, the term of this patent is extended or adjusted under 35 U.S.C. 154(b) by 0 days.

(21) Appl. No.: 10/608,321

(22) Filed: Jun. 27, 2003

(65) Prior Publication Data

US 2004/0000733 A1 Jan. 1, 2004

Related U.S. Application Data

(62) Division of application No. 09/845,425, filed on Apr. 30, 2001, now Pat. No. 6,769,767.

(51) Int. Cl.⁷ .......................... B29C 45/14; B29C 70/70
(52) U.S. Cl. .................. 264/250; 264/263; 264/272.11; 264/272.15
(58) Field of Search ............................ 264/250, 254, 264/259, 272.11, 272.15, 263, 272.14; 351/41, 158; 704/270, 271

(56) References Cited

U.S. PATENT DOCUMENTS

| 2,794,085 | A | * | 5/1957 | De Angelis | 200/61.58 R |
|---|---|---|---|---|---|
| 3,853,393 | A | * | 12/1974 | Fila et al. | 351/111 |
| 4,294,792 | A | | 10/1981 | Arons et al. | |
| 5,404,385 | A | * | 4/1995 | Ben-Haim | 377/24.2 |
| 5,594,511 | A | * | 1/1997 | Lin | 351/116 |
| 5,652,637 | A | * | 7/1997 | Marini | 351/116 |
| 5,717,479 | A | | 2/1998 | Rickards | |
| 5,949,516 | A | * | 9/1999 | McCurdy | 351/158 |
| 6,012,812 | A | * | 1/2000 | Rickards | 351/158 |
| 6,091,546 | A | * | 7/2000 | Spitzer | 359/618 |
| 6,099,117 | A | * | 8/2000 | Gregory | 351/49 |
| 6,163,926 | A | * | 12/2000 | Watanabe | 16/228 |
| 6,231,181 | B1 | * | 5/2001 | Swab | 351/116 |
| 6,311,155 | B1 | | 10/2001 | Vaudrey et al. | |
| 6,582,075 | B1 | * | 6/2003 | Swab et al. | 351/158 |
| 6,629,076 | B1 | * | 9/2003 | Haken | 704/271 |

OTHER PUBLICATIONS

Search results on BLUETOOTH from U.S. Trademark Electronic Search System.*
German Search Report dated Aug. 19, 2004.

\* cited by examiner

*Primary Examiner*—Angela Ortiz
(74) *Attorney, Agent, or Firm*—Joel Lutzker, Esq.; Anna Vishev, Esq.; Schulte Roth & Zabel LLP

(57) ABSTRACT

A wireless ad hoc pico network is formed by eyewear and other devices such as a computer, a bracelet and a telephone having similar transceivers mounted on them. The eyewear includes a frame and connected to the frame are two temples. Temples are connected to frame via hinges. Temples have a male portion of a connector incorporated in them. Female portion of the connector is made integral with the hinges. When the male portion is inserted in the female portion the temple is attached to the frame. The temples can be removed by pulling the connector apart, and a temple with different apparatus within it can be inserted in place of the removed temples. The temple may have co-molded within its body, an apparatus such as an audio device, a camera, a speaker, and a microphone, and a display device such as liquid crystal or an alarm.

7 Claims, 15 Drawing Sheets

FIG. 2b
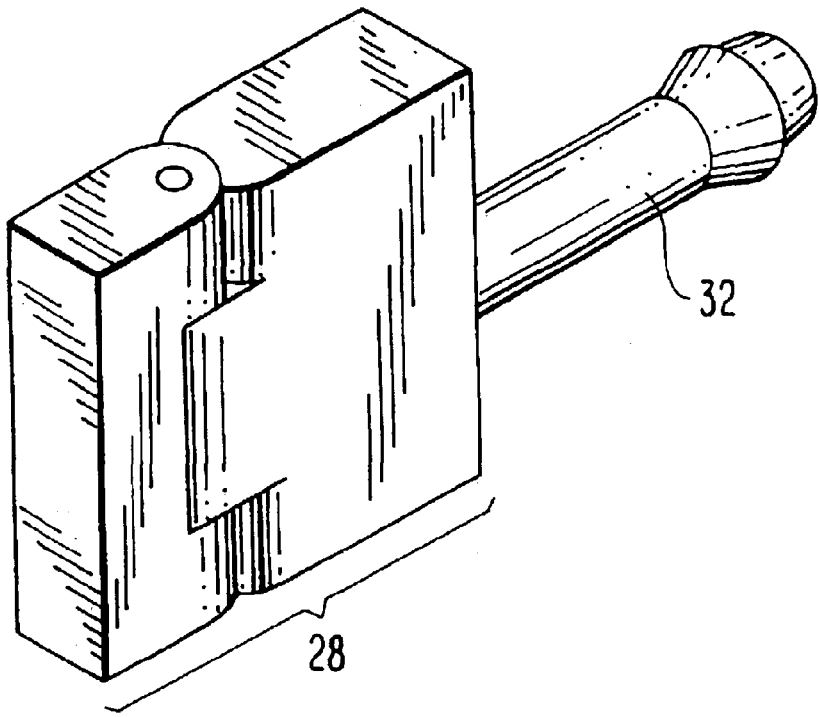
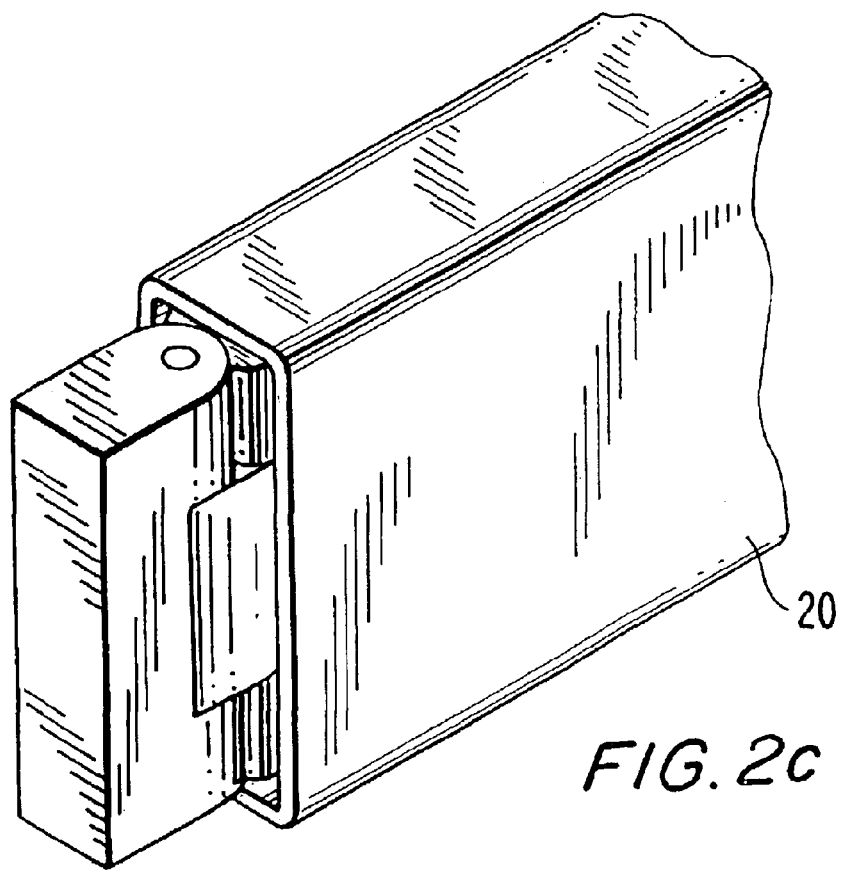
FIG. 2c

METHOD OF MANUFACTURING EYEWEAR

CROSS REFERENCE TO RELATED APPLICATIONS

This application is a divisional application of U.S. patent application Ser. No. 09/845,425 filed Apr. 30, 2001 now U.S. Pat. No. 6,769,767 claims all rights of priority thereto.

BACKGROUND OF THE INVENTION

1. Field of the Invention

The present invention relates to a wireless communication eyewear device having interchangeable temples. More particularly, the invention relates to eyewear having a transceiver enabled with small-range wireless communication technology.

2. Description of the Related Art

Many conventional wearable personal apparatus including eyewear, having electrical input-output devices are available to the consumers. Several of these apparatus provide wireless communications using radio frequency or infrared frequency. For example, U.S. Pat. No. 6,091,832 discloses a wearable personal apparatus that includes an audio transducer, which may function as an audio input or output device. The audio input or output signals are provided through a wireless system.

U.S. Pat. No. 6,091,546 discloses an eyeglass interface system which includes a display assembly and one or more audio and/or video assemblies mounted to an eyeglass frame. The display assembly is mounted to one temple and provides an image to be viewed by the user. The audio or video assembly is mounted on the other temple and is in communication with the display assembly. The audio or video assembly may comprise a camera assembly and/or an audio input or output assembly, such as microphone and/or speakers. Applications include hands-free telephone, hands-free pager, hands-free time display, hands-free blood pressure or vital sign monitoring device, hands-free voice conferencing or hands-free surveillance system. The applications can include voice recognition technology and/or GPS technology utilizing an infrared link or radio frequency (RF) link, or a fiber optic cable.

Additionally, a personal display device built into a frame of eyewear is disclosed at the website of inViso Inc. and may be found at the following URL address: www.inviso.com. The inViso's eyewear is designed in the shape of sunglasses with the built-in personal display device providing a wearer with a view of his/her computer screen. The displayed view is equivalent to a view provided by a 19-inch desktop monitor from a 2.5 feet distance. In order to display the content of the computer screen on the personal display device, however, the inViso's eyewear has to be plugged into the computer.

SUMMARY OF THE INVENTION

Conventional apparatuses are limited to handling a one to one communication, and can not form an ad hoc network consisting of more than two devices. Conventional audio devices do not function well in a noisy, radio environment and are bulky and have high power consumption. Therefore, it is desirable to provide a wireless communication device that is capable of forming an ad hoc network with a plurality of devices. It is also desirable to provide an apparatus that is low-cost, small in size, and has a low power consumption. It is also desirable to have an apparatus that can function in very noisy radio environments and is audible under severe conditions.

The present invention overcomes the shortcomings of the conventional apparatus, and provides a wireless network formed by connecting an eyewear with a computer, a bracelet and a telephone. The eyewear has a transceiver mounted on a temple. The computer, the bracelet and the telephone also have similar transceivers, mounted on them. Other devices, such as a radio, a CD player, a hand held global positioning satellite system and a heart rate monitor, having similar transceivers, can also be connected with the transceiver. The transceivers are preferably tiny, inexpensive, short-range transceivers that operate on globally available, unlicensed radio band, 2.45 gigahertz(GHz). The transceivers conform to the BLUETOOTH™ standard promoted by the BLUETOOTH™ Special Interest Group. BLUETOOTH™ is an open specification technology, whose specifications can be obtained from BLUETOOTH™ SIG, Inc. or downloaded from the following URL address: www.BLUETOOTH™.com. A copy of the BLUETOOTH™ Radio Specification is attached to the present specification and is fully incorporated herein by reference. The transceivers can support data speeds of up to 721 kilo-bits per second as well as three voice channels. The transceivers can operate at least two power levels: a lower power level that covers a range of about ten meters and a higher power level. The higher level covers a hundred-meter range, can function even in very noisy radio environments, and can be audible under severe conditions. The transceivers limit their output power to exactly that actually needed. If the receiving device is only a short distance away, the transceivers modify its signals to suit exact range. Furthermore, the radio automatically shifts to a low-power mode when traffic volume becomes low or stops. The power consumption of BLUETOOTH™ enabled devices is less than three percent of the power consumption of a mobile phone.

The invention contemplates eyewear with interchangeable temples housing a transceiver enabled with small-range wireless network technology, which allows the provided eyewear to form small-range ad-hoc networks with other devices equipped with similar transceivers.

The eyewear includes a frame and connected to the frame are two temples. The temples are connected to the frame hinges. The temples have a male portion of a connector, for example a one-eighth inch audio connector, incorporated in them. The female portion of the connector is made integral with the hinges. When the male portion is inserted into the female portion, the temple is attached to the frame. The temples can be removed by pulling the connector apart, and a temple with a different apparatus within it can be inserted in place of the removed temples.

In addition to housing a transceiver, each temple of the provided eyewear may have other communication devices, for example, an audio device, a camera, a speaker, a microphone, a display device such as a liquid crystal or an alarm device, co-molded within its body. A battery powering the transceiver and other co-molded devices can also be co-molded within one of the temples and connected to a co-molded device and the transceiver via a co-molded conductor.

In another embodiment, the eyewear, worn for example by an adult, comprises a distance alarm monitor to supervise the movement of a child. In this embodiment, a device, preferably in the form of a bracelet equipped with its own short-range transceiver, is worn by the child. The transceivers in the eyewear and the bracelet form a small-range wireless network, wherein the eyewear and the bracelet communicate with each other using signals conforming to the aforementioned BLUETOOTH™ standard. The transceiver in the eyewear is configured to activate the alarm when the distance between the bracelet and the eyewear exceeds a predetermined range.

Further features and advantages of the invention will become evident to one skilled in the art upon reading of the detailed description of the invention, which is given below by way of example only and with reference to the accompanying drawings.

BRIEF DESCRIPTION OF DRAWINGS

A full understanding of the invention can be gained from the following description of the preferred embodiments when read in conjunction with the accompanying drawings in which:

FIG. 2b is a diagram of the hinge with the male connector portion extending out before being molded into the temple;

FIG. 2c is a diagram showing the hinge molded into the temple;

DETAILED DESCRIPTION

Figure 1:
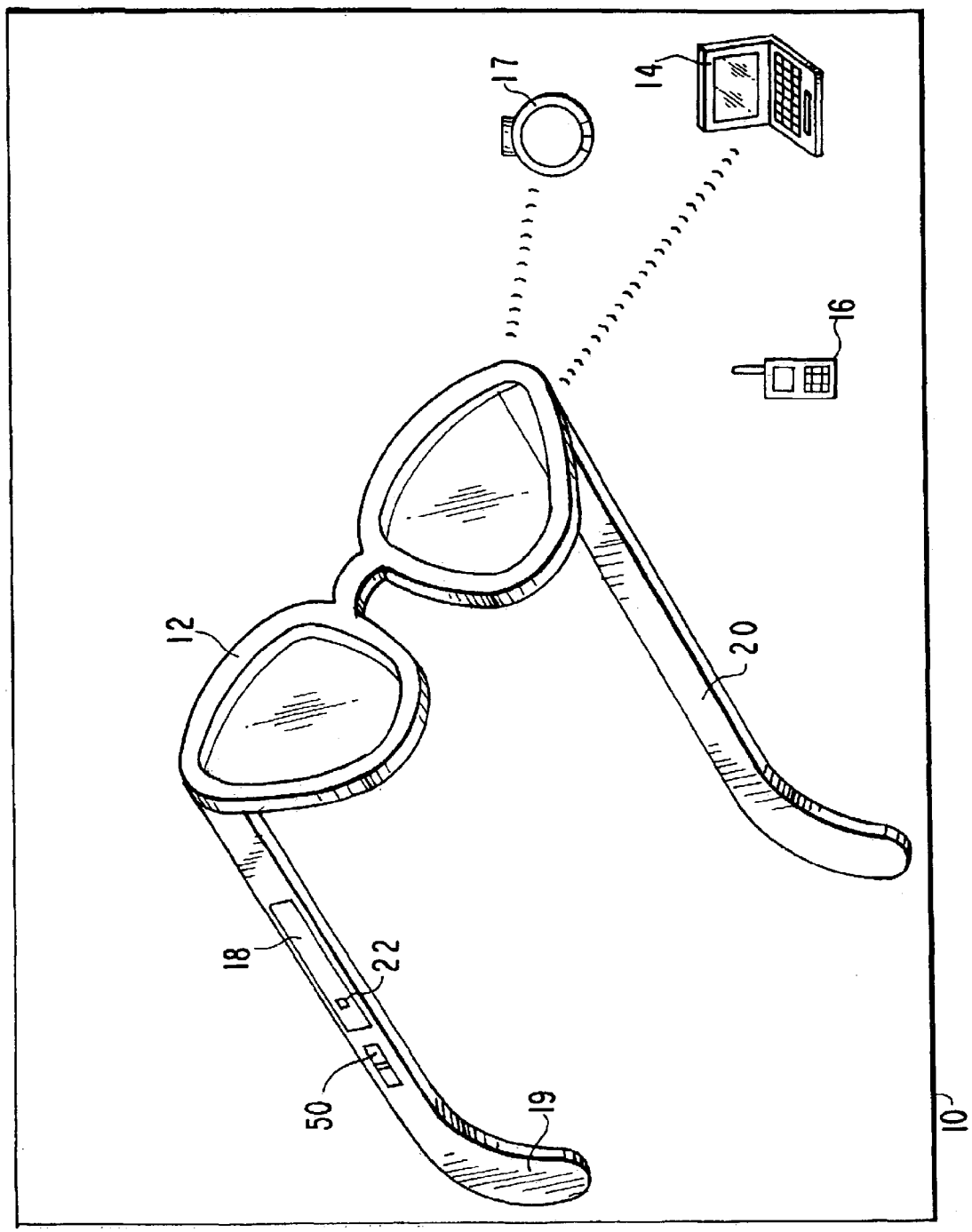
FIG. 1 is a schematic representation of a small-range wireless network formed by connecting an eyewear, constructed in accordance with the present disclosure, to a computer, a bracelet and a wireless telephone.

A general concept of the preferred embodiment of the present invention is shown in FIG. 1. In accordance with this embodiment, a wireless network 10 is formed by connecting eyewear 12 with computer 14, bracelet 17 and telephone 16. Eyewear 12 has a transceiver 18 mounted on one of the temples of the eyewear 12 (shown on the temple 19). Computer 14, bracelet 17 and telephone 16, also have similar transceivers, (not shown), mounted on them. When a user of the eyewear 12 comes within a predetermined distance from the above devices, the transceivers of the eyewear and these devices start to communicate to each other thereby creating the ad hoc small-range wireless network 10.

Transceiver 18 is a tiny, inexpensive, short range transceiver that operates on globally available, unlicensed radio band, 2.45 gigahertz(GHz). Transceiver 18 conforms to the BLUETOOTH™ standard. BLUETOOTH™ is an open specification technology, whose specifications can be obtained from BLUETOOTH™ SIG, Inc. or downloaded from the following URL address: www.BLUETOOTH™.com. A copy of the BLUETOOTH™ Radio Specification is attached to the present specification and is fully incorporated herein. Transceiver 18 can support data speeds of up to 721 kilo-bits per second as well as three voice channels. The transceiver can operate at a lower power level that covers about ten meters and a higher power level which covers about a hundred meters. Transceiver 18 includes a chip 22 that along with software control, allows the user to preset which units transceiver 18 can communicate with. The BLUETOOTH™ technology allows transceiver 18 to function even in very noisy radio environments, and be audible under severe conditions, for example, during a thunderstorm.

A connection between the eyewear 12 having the transceiver 18 and one or more of any other devices forms a small range wireless network 10, known as a piconet. Any device in the piconet, including the transceiver, can be configured to be a master, and the rest of the devices will be slaves. A different device may be configured to be the master at a different time, reverting the previous master to be a slave to the newly configured master. Several piconets can be established and linked together ad hoc, and a slave in one piconet can act as a master in another piconet. The clocks of all devices in the piconet are synchronized with the clock of the master. The full-duplex data rate within a multiple piconet structure with ten fully loaded, independent piconets can be more than 6 megabits per second.

Transceivers 18 and transceivers within other devices limit their output power to exactly that actually needed. If the receiving device is only a short distance away, the transceivers modify its signal to suit exact range. Furthermore, the radio automatically shifts to a low-power mode when traffic volume becomes low or stops. The low-power mode is interrupted by very short signal, with the purpose of verifying the established connection. BLUETOOTH™ enabled devices may have four modes of operation in a connection state. The four modes, in increasing order of power consumption are part, hold, sniff and active. Thus, the power consumption of BLUETOOTH™ enabled devices is less than three percent of the power consumption of a mobile phone.

Figure 2A:
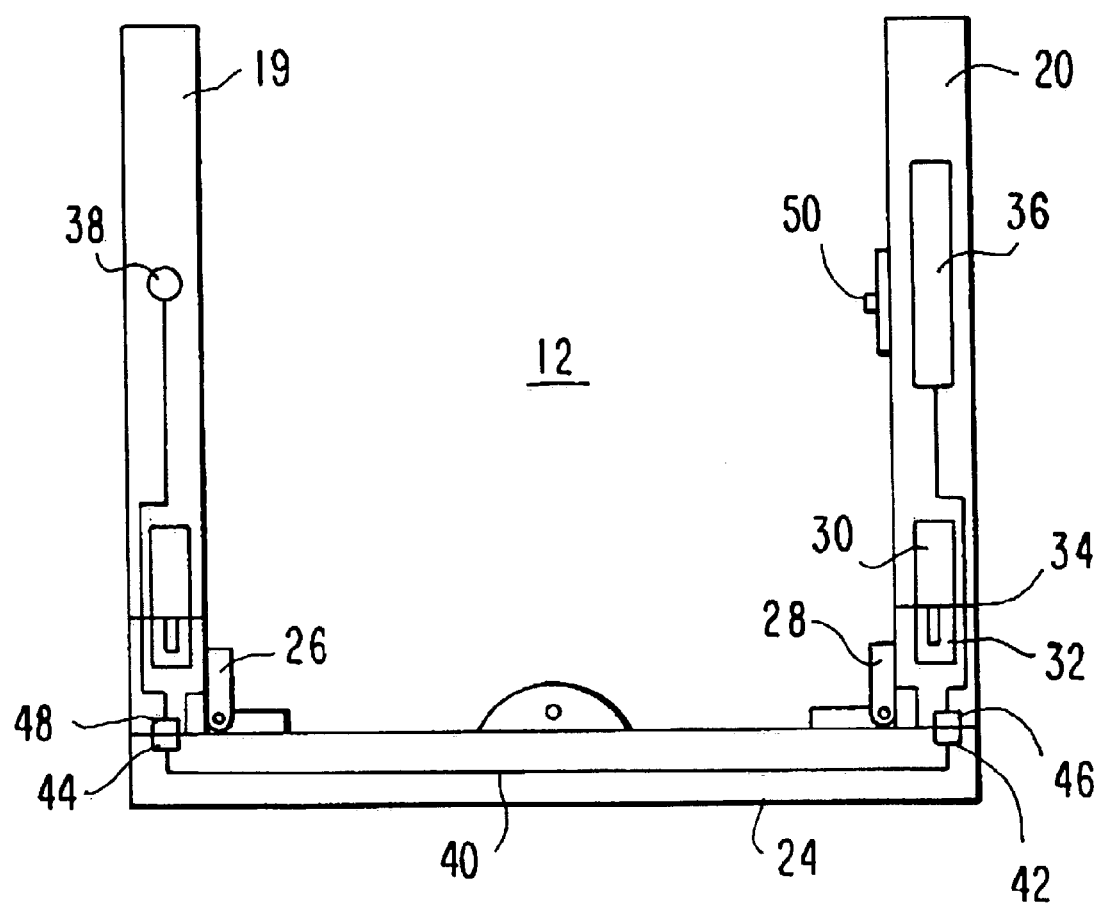
FIG. 2a is a schematic representation of the eyewear of FIG. 1 showing the removable temples of the eyewear and their connection to an eyewear frame.

Shown in FIG. 2a is a schematic representation of eyewear 12 of FIG. 1. Eyewear 12 includes a frame 24, and connected to frame 24 are two temples 19 and 20. Temples 19 and 20 are connected to frame 24 via hinges 26 and 28, respectively. Although hinges 26 and 28 are shown to be adjacent to and separate from connector portions of the eyewear, it should be appreciated that this is done for illustration purposes only. As discussed further with respect to FIGS. 2b–2f, in the preferred embodiment of the present invention each hinge is integral with one portion (either male or female) of the corresponding connector. Temples 19 and 20 each have a male portion 30 of a connector 34, for example, a one-eighth inch audio connector, incorporated in it. Female portion 32 of connector 34 is made integral with hinges 26 and 28. As it is evident to one skilled in the art, mounting positions of male portion 30 and female portion 32 may be reversed, as shown for example in FIGS. 2b–2f. When male portion 30 is inserted in female portion 32, temple 20 is attached to frame 24. Temple 19 is also attached to frame 24 in a similar manner. Temples 19 and 20 can be removed by pulling the connection apart, and a different temple having a different apparatus within it can be inserted in place of temples 19 or 20. Temples 19 and 20 when attached to frame 24 substantially hide hinges 26 and 28, thereby making eyewear 12 esthetically better. A patent application filed by Gregg T. Swab, entitled "Exchangeable Eyeglass Temple Pieces Utilizing Quick-Connect Attachment" Ser. No. 09/532,427, describes temple pieces with quick-connect attachment for quick attachment and removal of the temple pieces to the frame.

Frame 24 has pads 42 and 44 located near hinges 28 and 26, respectively. Temples 20 and 19 also have pads 46 and 48 which contact pads 42 and 44 respectively when temples 20 and 19 are in open position. The pads, when in contact, complete the electrical path thereby activating the circuits of apparatus 36. Alternatively, a switch 50 may be located on temples 19 or 20 to activate the circuits.

The connected hinge which permits electrical conduction between the both temples and the frame enables the sharing of functionality between the left and right temples. It further enables the battery and the circuitry such as the BLUETOOTH™ PCB to be on opposing sides to accommodate more circuitry and their functions and to balance the weight and volume. The hinge enables dual mono orstereo speakers and can accommodate USB devices such as a digital camera.

Figure 2D:
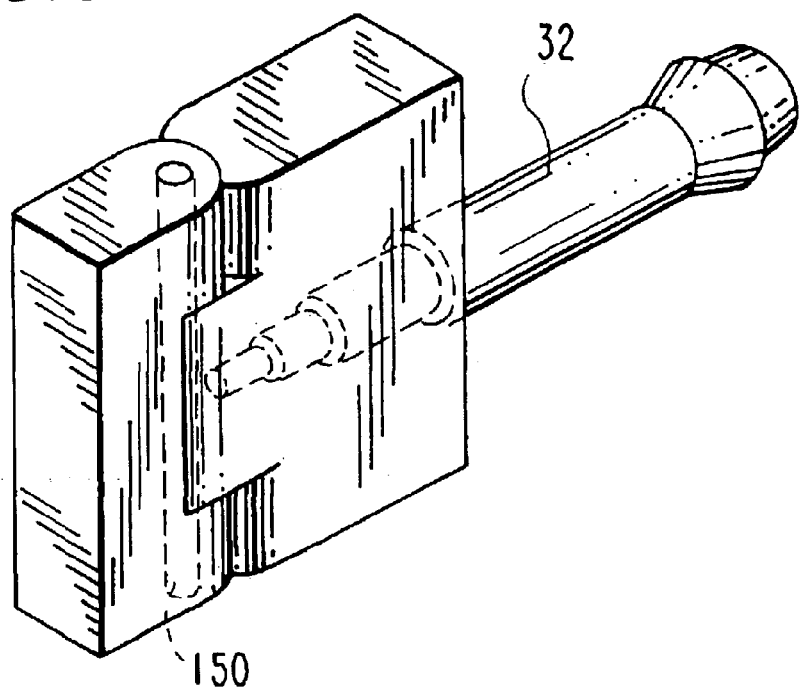
FIG. 2d is a diagram showing the spacial relationship of the pin of the hinge and the male connector portion.
Figure 2E:
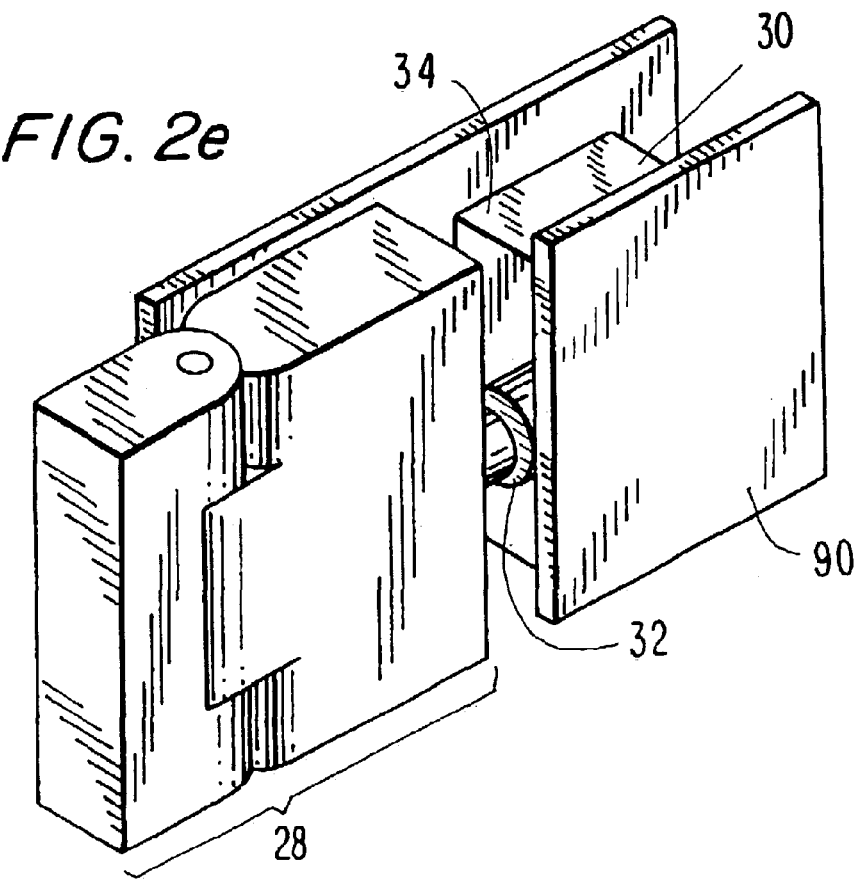
FIG. 2e is a diagram showing the hinge, connector and circuitry such a BLUETOOTH™ PCB before being molded into the temple.
Figure 2F:
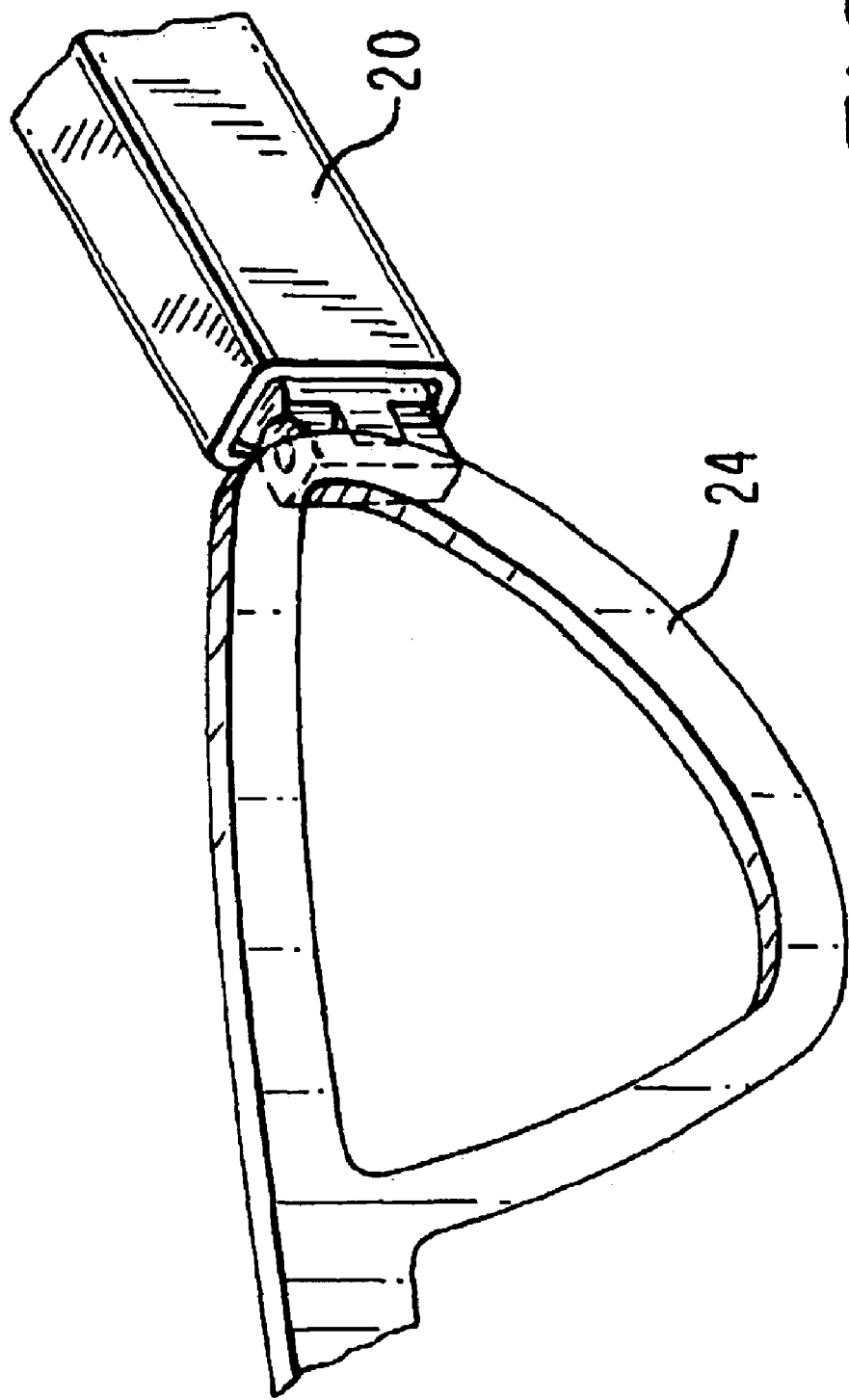
FIG. 2f is a diagram showing the spacial relationship of the assembly of FIG. 2c in the eyewear.

FIG. 2b is a diagram of the hinge (an embodiment of 26 or 28) with male connector portion 32 extending out before being molded into the temple 19, 20. FIG. 2c is a diagram showing the hinge molded into the temple. FIG. 2d is a diagram showing the spacial relationship of the pin 50 of the hinge and the male connector portion 32. FIG. 2e is a diagram showing the hinge, connector 34 and circuitry 90 such a BLUETOOTH™ PCB before being molded into the temple. FIG. 2f is a diagram showing the spacial relationship of the assembly of FIG. 2c in the eyewear.

Temple 20 has co-molded within its body, an apparatus 36. Apparatus 36 can be, for example, an audio device, a camera, a speaker, a microphone, and a display device such as a liquid crystal or an alarm. The apparatus includes electrical circuitry for operation in an electronics package such as a BLUETOOTH™ module with PCB. A battery 38, can be co-molded within temple 20 or 19 and connected to the co-molded apparatus 36 via co-molded conductors 40.

Figure 3:
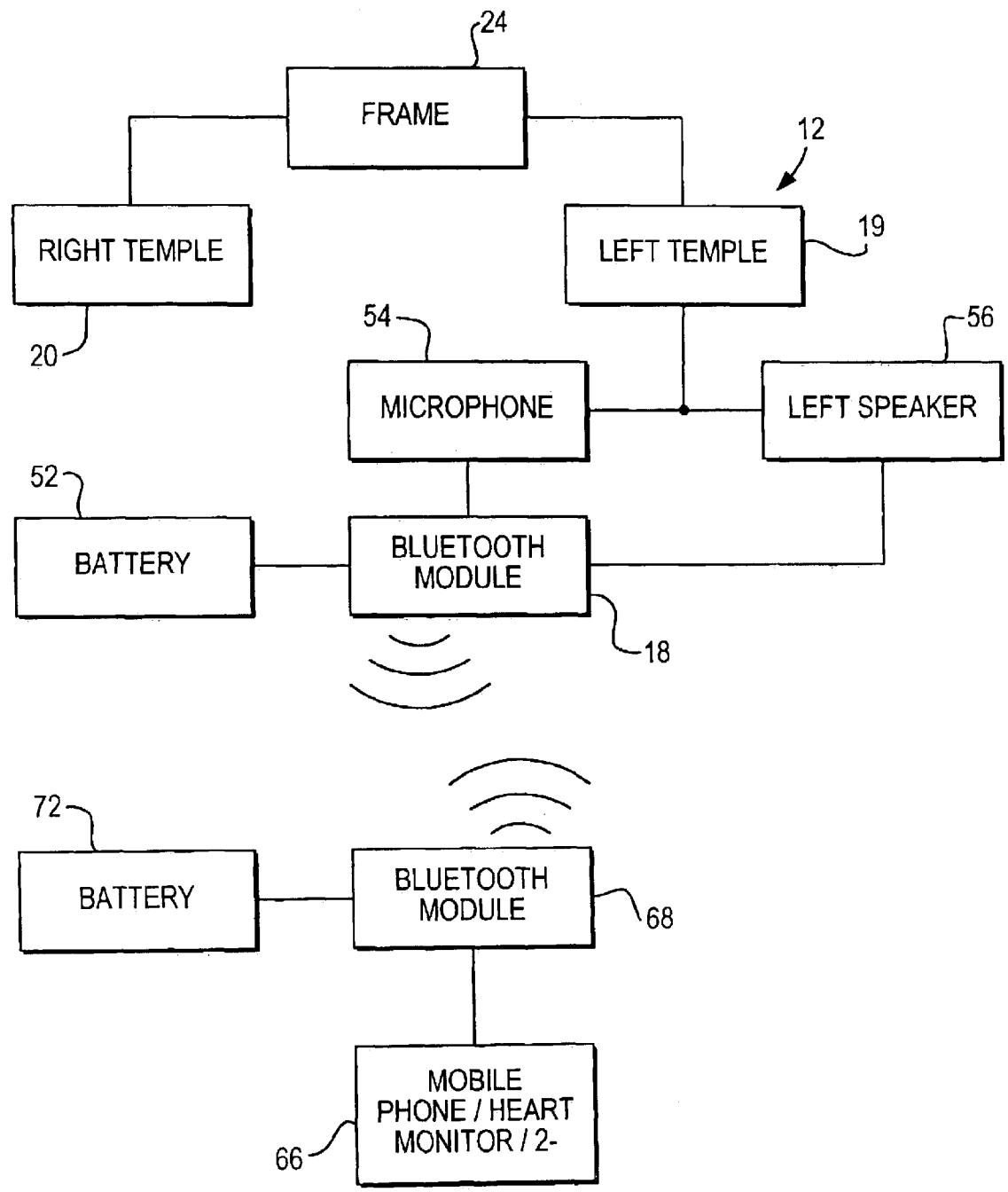
FIG. 3 is a flow chart of a network formed by the eyewear of the present invention and various communication devices, for example a mobile phone or a two-way radio.
Figure 7:
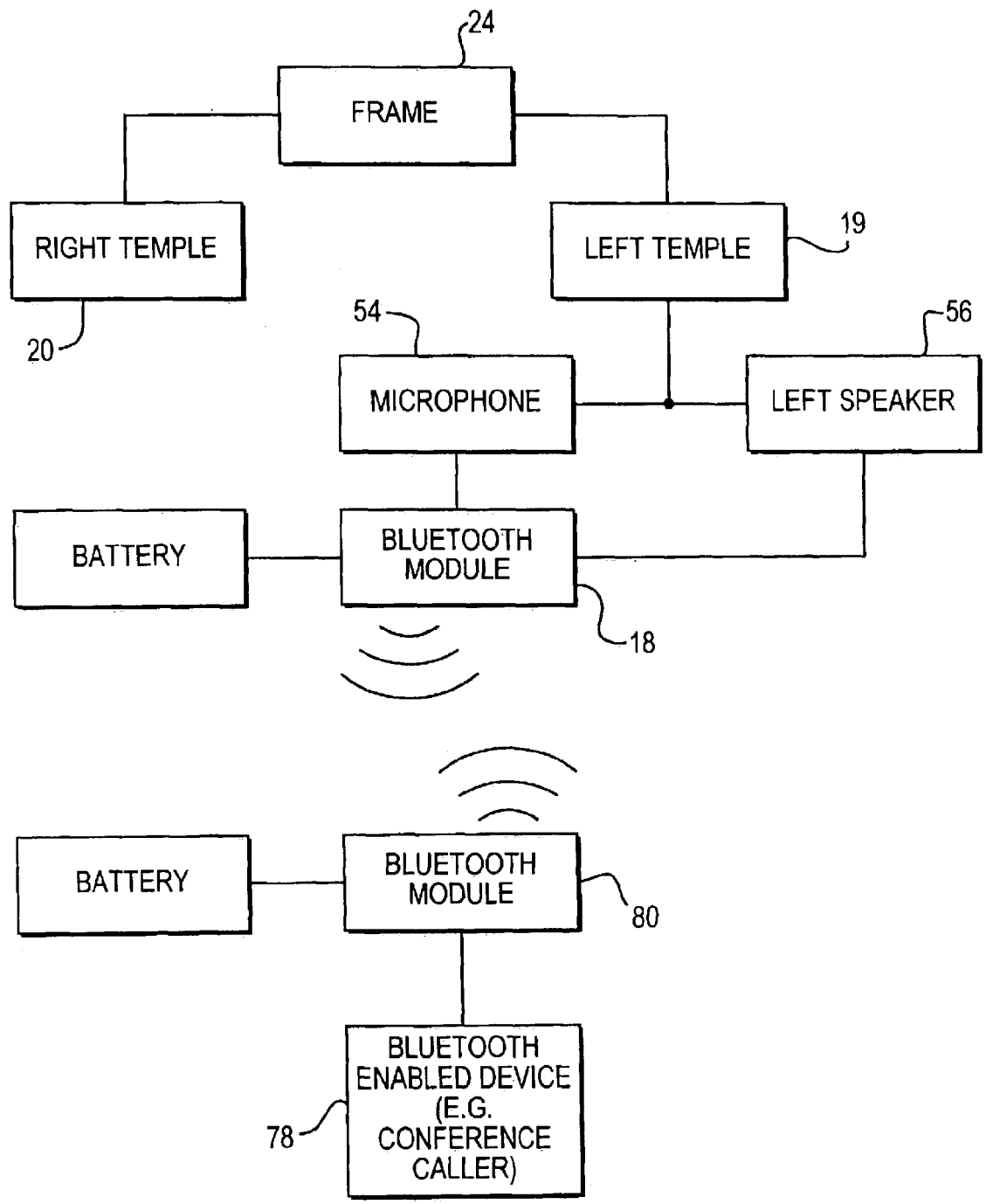
FIG. 7 is a flow chart of a network formed by the eyewear of the present invention and a telephone conferencing device.
Figure 12:
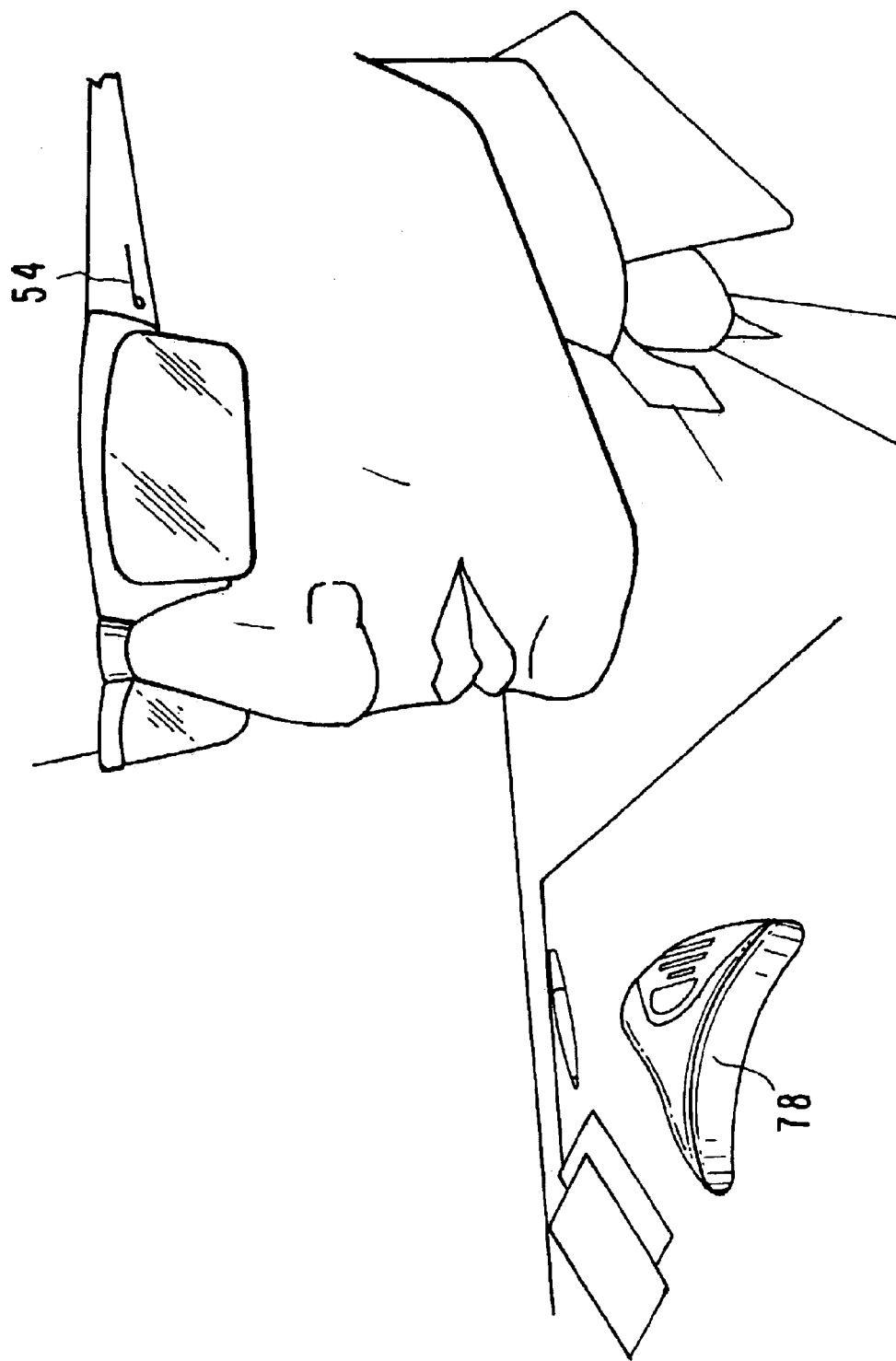
FIG. 12 is a schematic representation of the eyewear, having a microphone mounted on its temple, and a teleconferencing device being in communication with the eyewear.

Other devices, such as a radio, a CD player, a hand held global positioning satellite system and a heart rate monitor, having their own transceivers similar to the transceiver 18, can also be connected to the eyewear 12. As shown in the flow-chart of FIG. 3, in one embodiment of the present invention, the eyewear 12, having the transceiver 18, battery 52, microphone 54 and speaker 56 molded into one of its temples, is connected to a mobile phone, a heart rate monitor or a two-way radio, represented in the flow-chart as one box 66. All of these connected devices are equipped with their own transceivers 68, similar to the transceiver 18, and each transceiver is powered by a battery 72. Since mobile phones, heart-rate monitors and two-way radios are typically battery operated, no additional power source is required to power transceivers 68, A signal, for example audio information generated by the wearer of the eyewear 12, is transmitted through the microphone 54 and transceiver 18 to the transceiver 68 associated with the intended recipient device, which device, upon receipt of the signal, performs a desired action, for example further conveys the received audio information. A similar embodiment of the present invention is shown in FIGS. 7 and 12 where the eyewear 12 is utilized in connection with telephone conferencing equipment 78. The transceiver 18 of the eyewear 12 is then coupled to the transceiver 80 of the telephone conferencing equipment 78 for transmission/receipt of communication signals. This embodiment of the present invention may also be utilized together with a digital camera, as described more fully below, for video conferencing.

Figure 4:
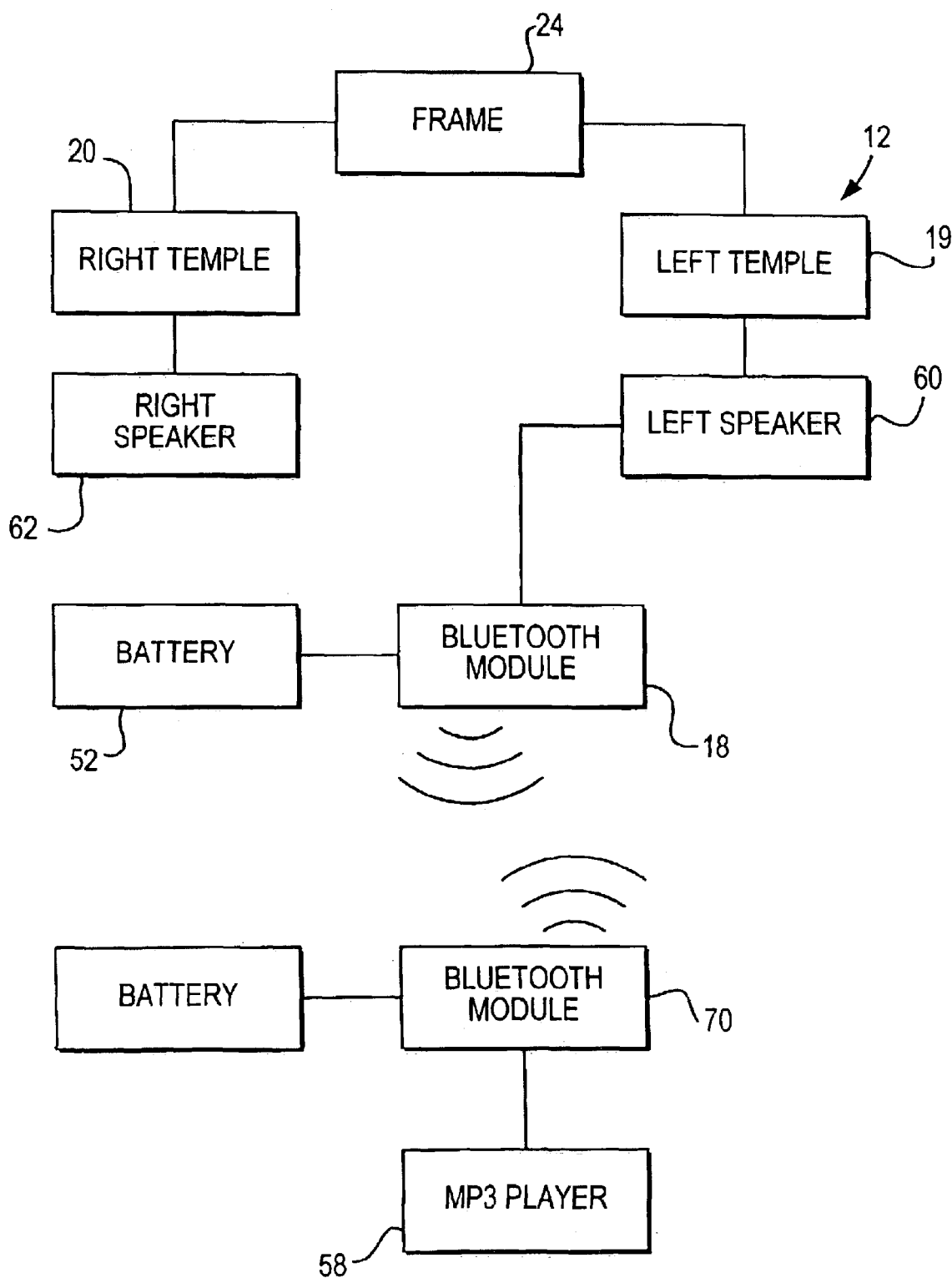
FIG. 4 is a flow chart of a network formed by the eyewear of the present invention and various audio-playing devices such as an MP3 player.
Figure 9:
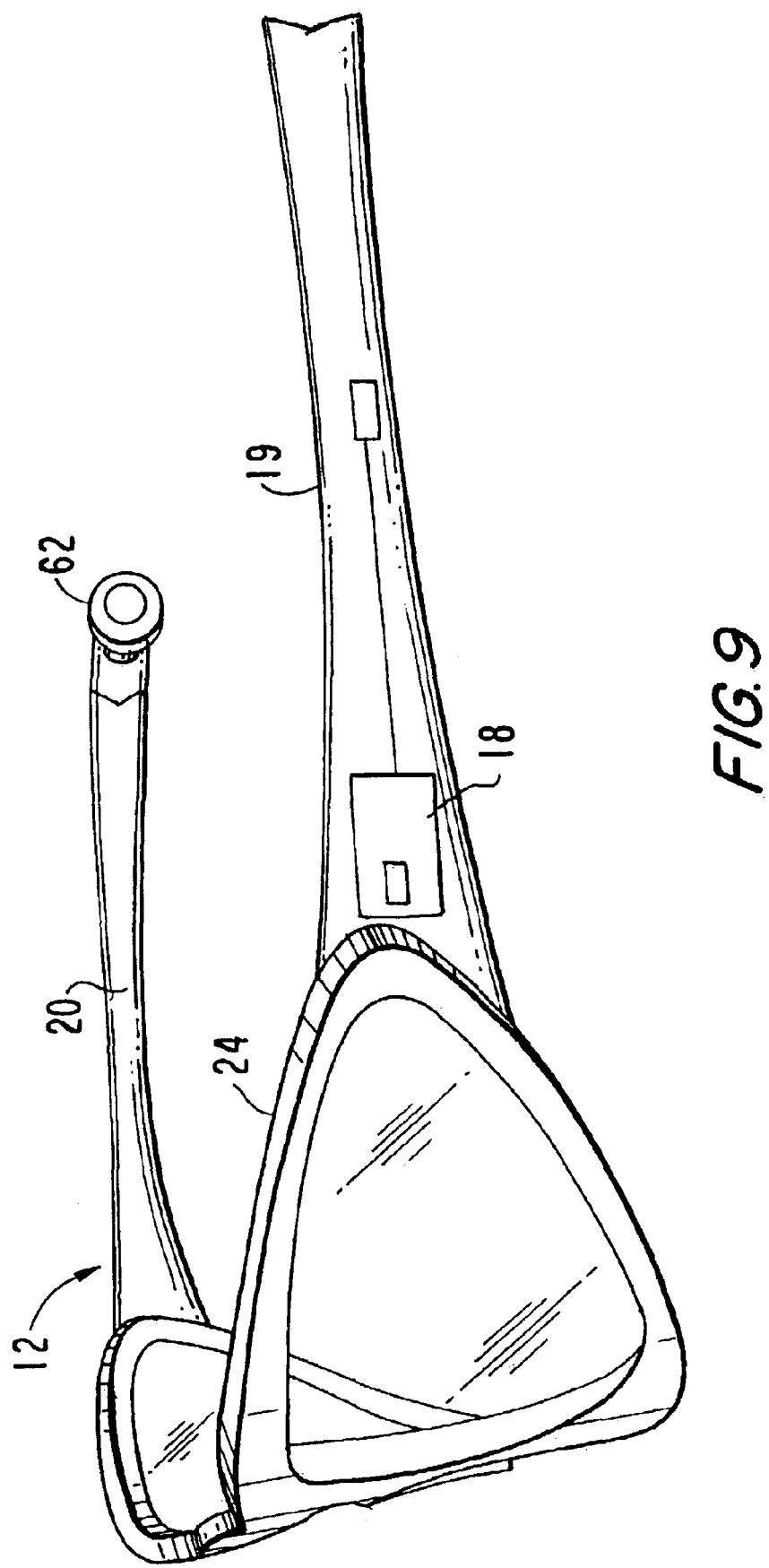
FIG. 9 is a side perspective view of the eyewear provided with a transceiver and a pair of removable audio speakers.
Figure 10:
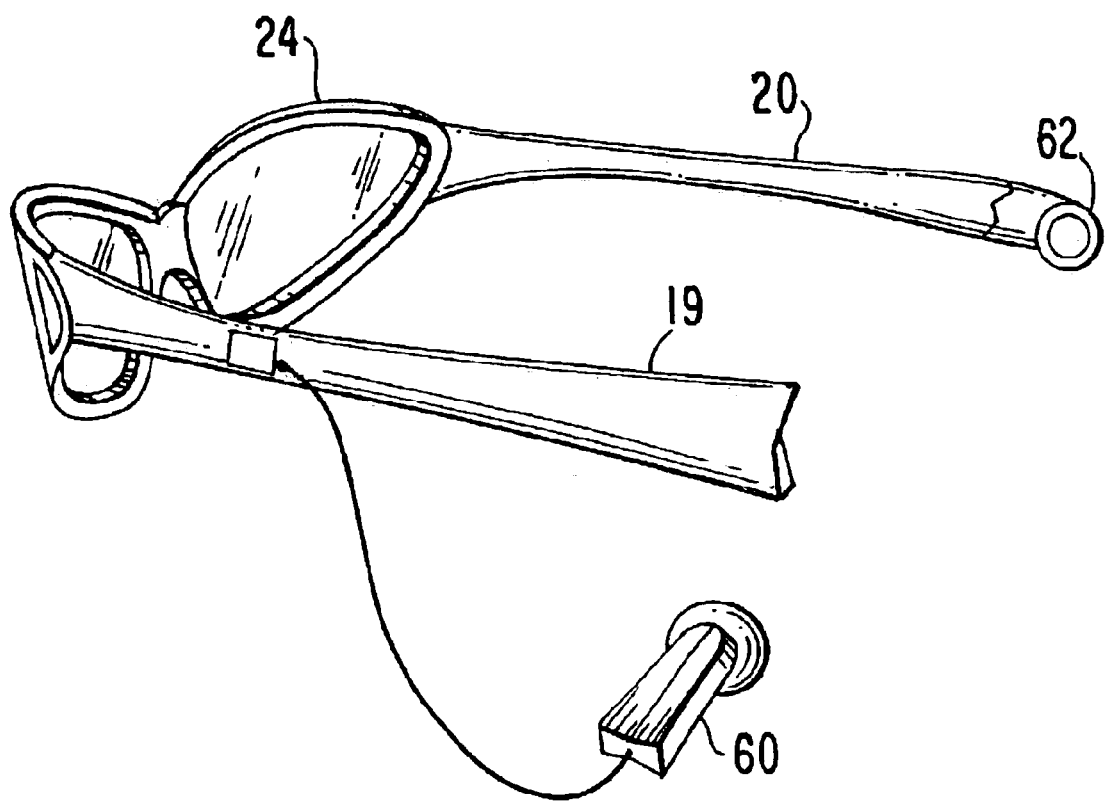
FIG. 10 is a back perspective view of the eyewear shown in FIG. 8 with one of the speakers being removed from its temple.

In another embodiment of the present invention, the eyewear 12 may be connected to various audio-playing devices, for example, an MP3 audio player 58, through the eyewear transceiver 18 coupled to the MP3 player's transceiver 70, as shown in the flow-chart of FIG. 4. In this embodiment, one speaker is mounted on each temple of the eyewear 12, i.e., a left speaker 60 is mounted on the left temple 19 and a right speaker 62 is mounted on the right temple 20. Preferably, only one speaker (left speaker 60 in FIG. 4) is connected directly to the transceiver 18, the other speaker (right speaker 62 in FIG. 4) is then connected to the first speaker through the electrically conductive connection of the two temples and the frame. Similarly to the above described embodiment, the MP3 player 58 is equipped with its own transceiver 70 capable of exchanging signals with the transceiver 18. In operation, when MP3 player plays back previously stored music or any other stored audio signal, the transceiver 70 feeds this signal to the transceiver 18 which, in turn, conveys the signal to the speakers 60 and 62. This embodiment of the present invention is further illustrated in FIGS. 9–10 showing the eyewear 12 having the transceiver 18 molded into the left temple 19, the left speaker 60 removably mounted on the left temple 19 and the right speaker 62 removably mounted on the right temple 20. Left temple 19, frame 24 and right temple 20 form an electrically conductive link connecting the right speaker 62 to the left speaker 60.

Figure 5:
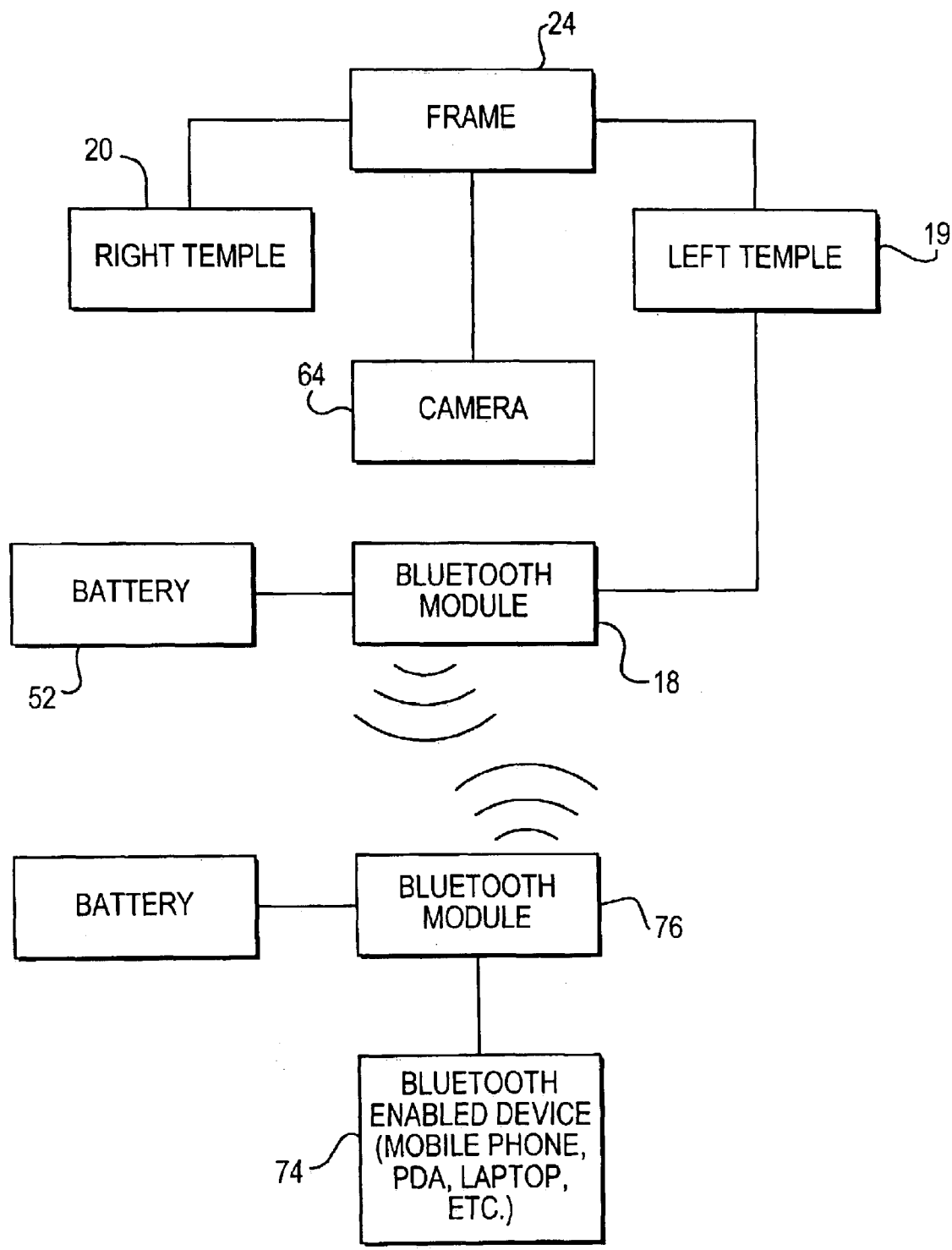
FIG. 5 is a flow chart of a network formed by the eyewear having a camera mounted on its frame and various video-enabled devices, for example, a personal digital assistant (PDA) or a laptop computer.
Figure 6:
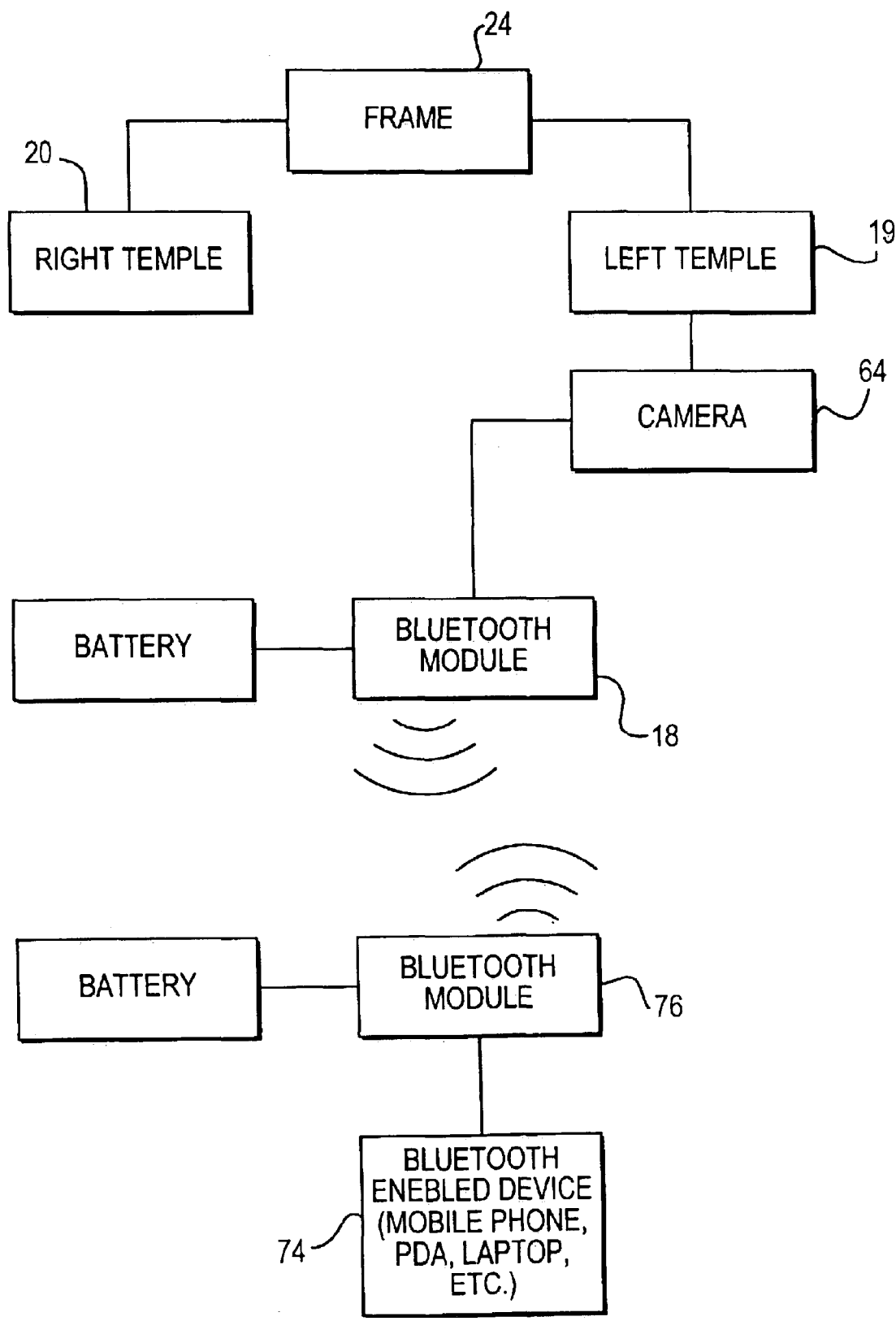
FIG. 6 is a flow chart of a network formed by the eyewear having a camera mounted on one of its temples and various video-enabled devices, for example, a personal digital assistant (PDA) or a laptop computer.
Figure 11:
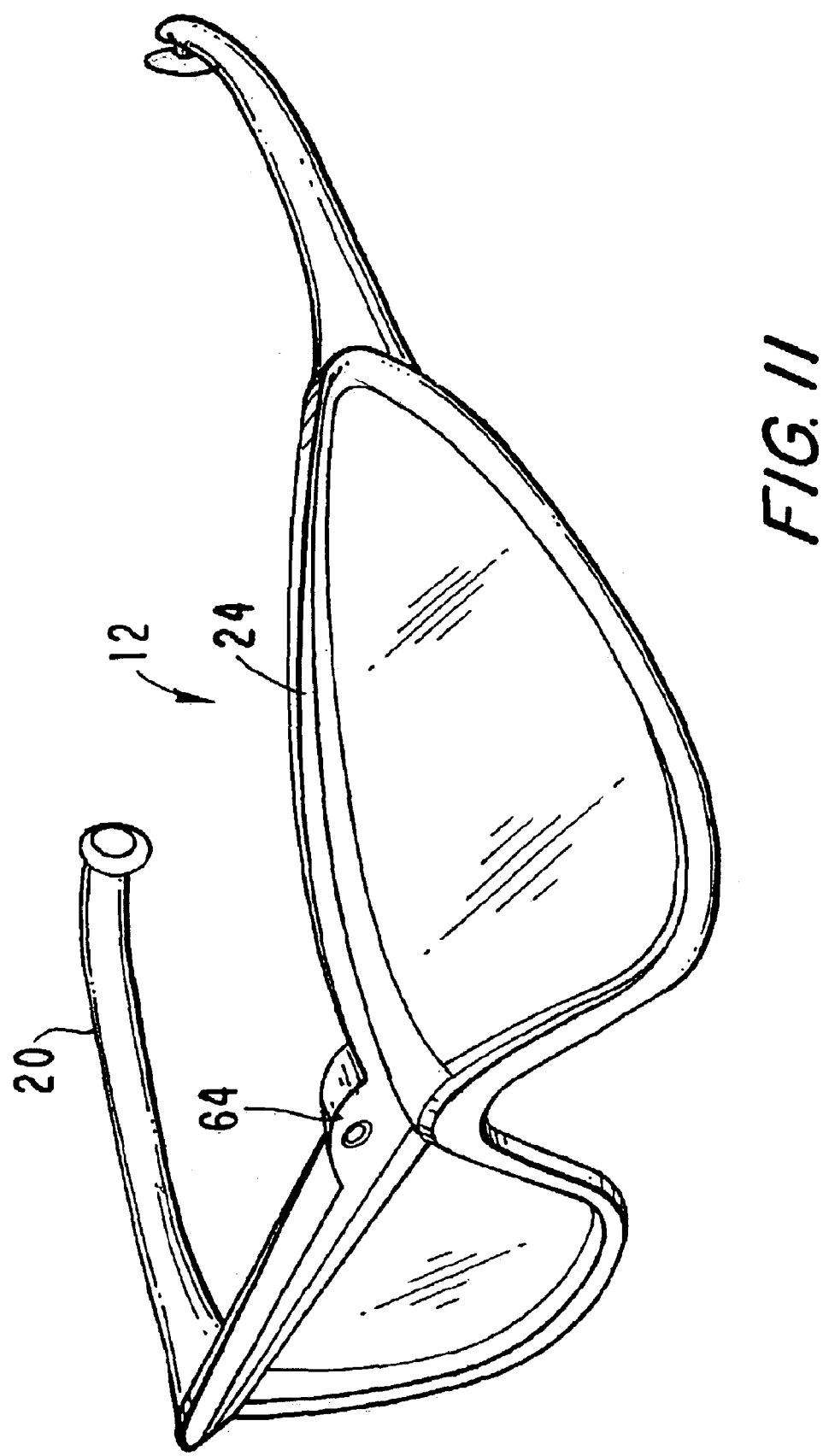
FIG. 11 is a front perspective view of the eyewear provided with a digital camera mounted on the frame of the eyewear and a pair of speakers mounted on the temples.

Various video or photo-enabled devices 74, such as a laptop, personal digital assistant (PDA), mobile phone or others, can also be connected to the eyewear 12, as shown in the flow-chart of FIG. 5. In this embodiment, a small digital camera 64 is mounted on the frame 24 of the eyewear 12, as shown for example in FIG. 11. Camera 64 can preferably take digital still pictures as well as video images and transmit them through the transceiver 18 to one or several transceivers 76 of the connected devices 74. If camera 64 is provided with software, such software may be stored on one of the connected devices 74, for example the laptop computer. It is possible then to control camera 64 by transmitting commands, issued from the laptop computer, through the laptop's transceiver 76 to the eyewear's transceiver 18, which then conveys the commands to the camera for fulfillment. This embodiment may be particularly useful if utilized together with the child's alarm system described below. In the described embodiment, the electrically conductive connection of the two temples and the frame is necessary in order for the signal to be conveyed to and from the connected devices. However, if such connection is not desirable, camera 64 may be located on the same temple, for example temple 19, with the transceiver 18. An electrical connection link between the camera and the transceiver may then be embodied within the single temple, as shown in the flowchart of FIG. 6.

Figure 8:
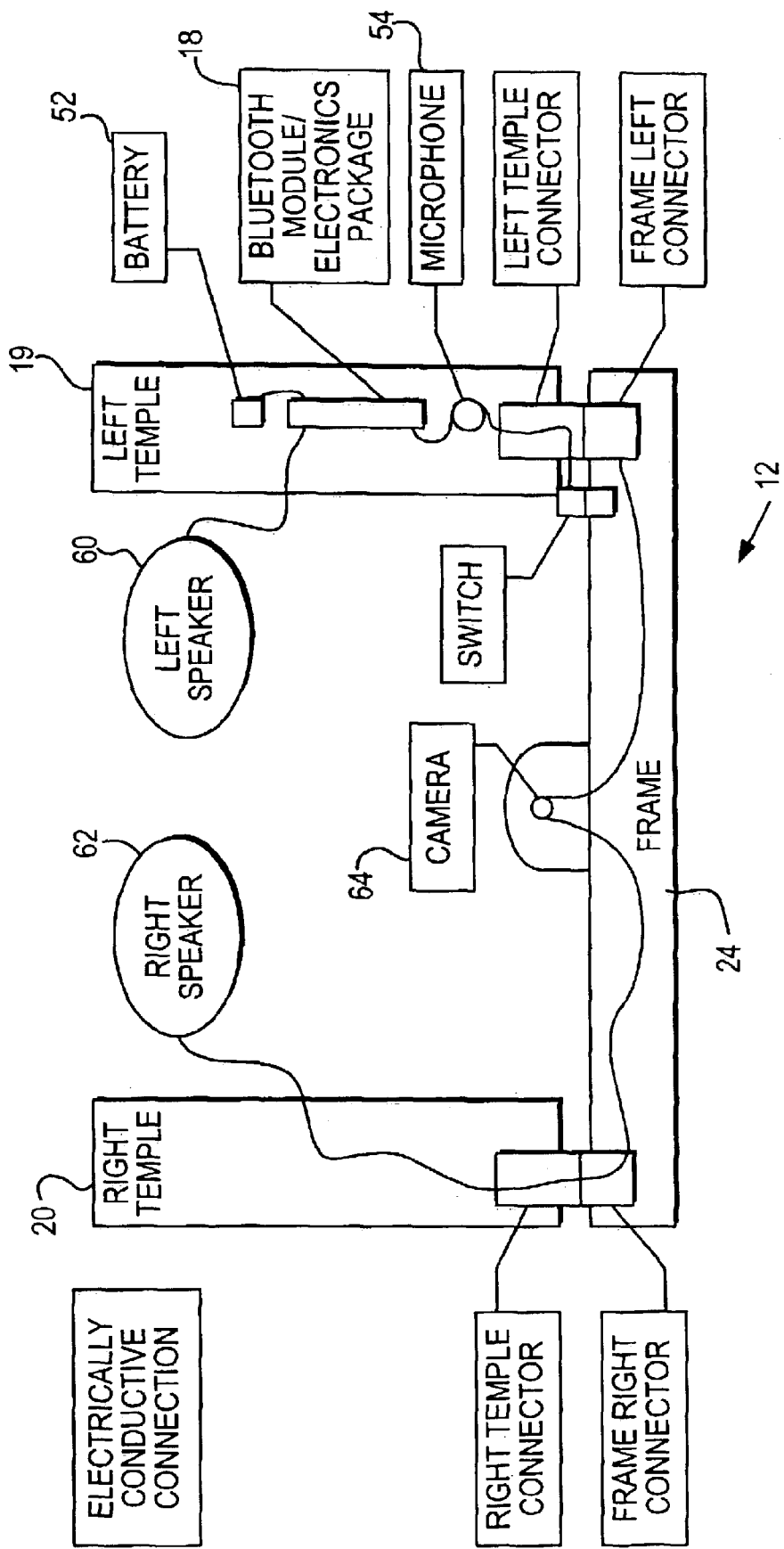
FIG. 8 is a schematic diagram of different components of the eyewear co-molded within the frame and temples of the eyewear.

FIG. 8 illustrates a possible combination of the eyewear components described in the previous embodiments. As described above, the eyewear comprises the frame 24 and two temples: left temple 19 and right temple 20. Frame 24 preferably houses the camera 64 for taking video images and still photographs. Right temple 20 preferably houses a removable right speaker 62. Left temple 19 preferably houses a removable left speaker 60, microphone 54, transceiver 18 and battery 52. When the eyewear 12 is open, as shown in FIG. 8, the electrical circuit of the conductive connection between all the components is closed, thereby enabling battery 52 to power all of the components located on the frame and the opposite temple.

In another embodiment, eyewear 12 worn for example by an adult, comprises a distance alarm monitor to supervise the movement of a child. In this embodiment, a device, preferably in the form of a bracelet 17 equipped with its own short-range transceiver (see FIG. 1), is worn by the child. Transceiver 18 in the eyewear and transceiver in the bracelet 17 form a small-range wireless network, wherein the eyewear and the bracelet communicate with each other using signals conforming to the aforementioned BLUETOOTH™ standard. The transceiver 18 in the eyewear 12 is configured to activate the alarm when the distance between the bracelet 17 and the eyewear 18 exceeds a predetermined range. The alarm could be, for example, a video alarm like a red light, or an audio alarm like an audible beep or vibratory alarm. Of course the functions of the eyewear and the bracelet may be reversed, i.e. the bracelet with a distance alarm monitor is worn by the supervising adult and the eyewear with its own transceiver is worn by the child. Alternatively, two pairs of eyewear may be provided, one with an alarm monitor and a controlling transceiver, to be worn by the adult, and another with a controlled transceiver, to be worn by the child.

The invention also includes the methods of manufacturing the eyewear. The eyewear is manufactured in a process to create electrical components contained throughout the entire frames and temples. Electrical components discussed above and electrical conductors are embedded in the temple and frame portions for the purpose of supplying electrical energy to the various components. In one method some or all of the components, including the conductive wires are co-molded into the temples and frames. This is an in-process method where the components are inserted into the temple and frame tools. The mold cycle is started, plastic material flows into the core and covity of the tool, and the components are permanently set in the rigid temples and frames.

Alternatively, the method of manufacture may be that some or all of the components, including the conductive wires, are assembled into piece parts that make up the temples and frames. The piece parts that make up the temples and frames are designed and injection molded to facilitate easy insertion and assembly of mechanical and electrical components. Further, a combination of the co-molded and assembled components may be used to maximize efficiency.

While particular embodiments of the present invention have been described, it will be apparent to those skilled in the art that changes and modifications may be made without departing from this invention in its broader aspect and, therefore, the appended claims are to encompass within their scope all such changes and modifications that fall within the true sprit and scope of this invention.

We claim:

1. A method of manufacturing eyewear comprising the steps of:

molding a frame;

molding a temple;

co-molding components of an apparatus in said temple;

co-molding a wireless radio frequency transceiver for short-distance wireless communication in said eyewear;

forming a connector by erecting a male connector portion projecting from one of said frame and said temple, providing a female connector portion within the other of said frame and said temple; and removably connecting said frame with said temple using said connector by removably inserting said male connector portion into said female connector portion, and securing said male connector portion within said female connector portion, such that the insertion of said male connector portion into said female connector portion both releasably attaches said temple to said frame and establishes an electrical connection between said frame and said temple.

2. The method of claim 1 further comprising the step of:

co-molding conductors in said temple and said frame, said conductors making electrical connection between said components located in said temple and said frame or said temples.

3. The method of claim 1, wherein said apparatus is selected from a group consisting of an audio device having a speaker and a microphone, a camera, a display device, a distance alarm and an ear bud.

4. The method of claim 1 further comprising the step of co-molding said wireless radio frequency transceiver in said temple.

5. The method of claim 4, wherein said wireless radio frequency transceiver is capable of forming an ad hoc wireless network with a plurality of devices.

6. The method of claim 1 further comprising the step of co-molding said wireless radio frequency transceiver in said frame.

7. The method of claim 6, wherein said wireless radio frequency transceiver is capable of forming an ad hoc wireless network with a plurality of devices.

\* \* \* \* \*